United States Patent
Offerdahl et al.

(10) Patent No.: US 11,751,851 B2
(45) Date of Patent: Sep. 12, 2023

(54) METHODS, SYSTEMS AND COMPUTER PROGRAM PRODUCTS FOR TISSUE ANALYSIS USING ULTRASONIC BACKSCATTER COHERENCE

(71) Applicant: Duke University, Durham, NC (US)

(72) Inventors: Katelyn Offerdahl, Durham, NC (US); Gregg Trahey, Durham, NC (US)

(73) Assignee: Duke University, Durham, NC (US)

( * ) Notice: Subject to any disclaimer, the term of this patent is extended or adjusted under 35 U.S.C. 154(b) by 51 days.

(21) Appl. No.: 17/462,548

(22) Filed: Aug. 31, 2021

(65) Prior Publication Data
US 2023/0066217 A1 Mar. 2, 2023

(51) Int. Cl.
*A61B 8/08* (2006.01)
*G16H 50/70* (2018.01)

(52) U.S. Cl.
CPC ............. *A61B 8/485* (2013.01); *A61B 8/08* (2013.01); *A61B 8/5207* (2013.01); *G16H 50/70* (2018.01)

(58) Field of Classification Search
CPC .......... A61B 8/485; A61B 8/08; A61B 8/5207
See application file for complete search history.

(56) References Cited

U.S. PATENT DOCUMENTS

| | | |
|---|---|---|
| 6,371,912 B1 | 4/2002 | Nightingale et al. |
| 6,764,448 B2 | 7/2004 | Trahey et al. |
| 6,951,544 B2 | 10/2005 | Trahey et al. |
| 8,118,744 B2 | 2/2012 | Palmeri et al. |
| 2007/0054282 A1* | 3/2007 | Liew .................... C12Q 1/6809 435/6.11 |
| 2013/0109971 A1* | 5/2013 | Dahl .................... G01S 7/52046 600/447 |
| 2020/0205786 A1* | 7/2020 | Labyed .................... A61B 8/54 |
| 2020/0359991 A1 | 11/2020 | Xu et al. |
| 2022/0346749 A1* | 11/2022 | Pernot ..................... G01H 5/00 |

FOREIGN PATENT DOCUMENTS

CN 105266851 A * 1/2016
WO 2021058731 A1 4/2021

OTHER PUBLICATIONS

English translation of CN-105266851 (Year: 2016).*
Jeremy Paige, "A Pilot Comparative Study of Quantitative Ultrasound, Conventional Ultrasound, and MRI for Predicting Histology-Determined Steatosis Grade in Adult Nonalcoholic Fatty Liver Disease", May 2017 (Year: 2017).*
Yingzhen Zhang, "Liver fat imaging—a clinical overview of ultrasound, CT, and MR imaging", 2018 (Year: 2018).*

(Continued)

*Primary Examiner* — Katherine L Fernandez
*Assistant Examiner* — Brooke Lyn Klein
(74) *Attorney, Agent, or Firm* — Myers Bigel, P.A.

(57) ABSTRACT

Methods, systems and computer program products for determining a property for a sample having a target region using ultrasound data from an ultrasound scanner include generating at least one spatial coherence curve based on ultrasound backscatter data in the target region, the spatial coherence curve comprising coherence values as a function of depth in the sample; and determining a property for a sample in response to the spatial coherence curve as a function of depth.

17 Claims, 7 Drawing Sheets

(56) References Cited

OTHER PUBLICATIONS

Bottenus, et al., "Acoustic reciprocity of spatial coherence in ultrasound imaging", IEEE Transactions on Ultrasonics, Ferroelectrics, and Frequency Control, 62(5), 21015, 852-861.
Li, et al., "Angular coherence in ultrasound imaging: Theory and applications", The Journal of the Acoustical Society of America, 141(3), 2017, 1582-1594.
Mallart, et al., "The van Cittert-Zernike theorem in pulse echo measurements", The Journal of the Acoustical Society of America, 90(5), 1991, 2718-2727.
Walker, et al., "Speckle coherence and implications for adaptive imaging", The Journal of the Acoustical Society of America, 101(4), 1997, 1847-1858.
International Search Report and Written Opinion corresponding to PCT/US2022/075328, dated Nov. 30, 2022, (18 pages).
Offerdahl, et al., "Occult Regions of Suppressed Coherence in Liver B-Mode Images", Ultrasound in Medicine & Biology, 48(1), 2022, 47-58.
Pinton, et al., "Spatial Coherence in Human Tissue: Implications for Imaging and Measurement", IEEE Transactions on Ultrasonics, Ferroelectrics, and Frequency Control, 61(12), 2014, 1976-1987.

\* cited by examiner

FIG. 5C

METHODS, SYSTEMS AND COMPUTER PROGRAM PRODUCTS FOR TISSUE ANALYSIS USING ULTRASONIC BACKSCATTER COHERENCE

FIELD OF THE INVENTION

The present invention relates to tissue analysis using ultrasonic backscatter coherence, and in particular, to quantification of tissue using ultrasonic backscatter coherence as a function of depth.

BACKGROUND

Non-alcoholic fatty liver disease (NAFLD) is a chronic diffuse liver disease that is a widespread and increasingly prevalent public health problem with deleterious societal and financial impacts. The current gold standard for evaluating liver disease is a liver biopsy. Biopsy studies can be used to measure liver fat content, inflammation, and fibrosis. However, liver biopsies may be inaccurate if there is a sampling error, and it is not viable for widespread use due to its associated morbidity, mortality and poor patient compliance. Magnetic resonance imaging methods have shown promise in the characterization of some components of NAFLD; however, the cost and lack of availability of magnetic resonance imaging facilities have limited their impact on patient care.

Ultrasonic imaging, including radiation force-based methods, are a low costs, more widely available modality that is now used in NAFLD diagnosis and staging. Other conventional ultrasound imaging used for screening of suspected NAFLD include evaluating liver stiffness using ultrasound elastography, including strain elastography and shear wave elastography, which uses acoustic radiation force induced tissue displacement. However, ultrasound techniques may be challenging in cases of obese patients and its difficulty in its quantification or characterization of liver fat content. Ultrasound imaging techniques may also yield ambiguous results in patients with significant fibrosis.

SUMMARY OF EMBODIMENTS OF THE INVENTION

In some embodiments, a method for determining a property for a sample having a target region using ultrasound data from an ultrasound scanner includes generating at least one spatial coherence curve based on ultrasound backscatter data in the target region, the spatial coherence curve comprising coherence values as a function of depth in the sample; and determining a property for a sample in response to the spatial coherence curve as a function of depth.

In some embodiments, the sample comprises in vivo liver tissue and the property comprises an estimation of fatty tissue or liver health. The estimation of fatty tissue or liver health may be based on an experimental model of actual clinical data comprising spatial coherence curves for clinical values of fatty tissue or liver health. The estimation of fatty tissue or liver health can indicate increased fatty tissue percentage or decreased liver health based on decreasing coherence values as a function of greater depth in the in vivo liver tissue. In some embodiments, determining a property for a sample in response to the spatial coherence curve as a function of depth further comprises fitting a curve to the spatial coherence curve for the liver tissue, and the property is determined based on a correlation between a curve fit value and known curve fit values for the experimental model of actual clinical data. The estimation of fatty tissue or liver health may include early stage steatosis.

In some embodiments, the experimental model of actual clinical data comprises a first set of spatial coherence curves for clinical values of fatty tissue or liver health corresponding to late-stage steatosis above a threshold steatosis value, and a second set of spatial coherence curves for clinical values of fatty tissue or liver health corresponding to early-stage steatosis below the threshold steatosis value, and the method includes determining whether the sample is above or below the threshold steatosis value based on ultrasound elastography.

In some embodiments, the estimation of fatty tissue or liver health is determined based on the first set of spatial coherence curves if the ultrasound elastography indicates a steatosis value above the threshold steatosis value, and the estimation of fatty tissue or liver health is based on the second set of spatial coherence curves if the ultrasound elastography indicates a steatosis value below the threshold steatosis value.

In some embodiments, a computer program product for determining a property for a sample having a target region using ultrasound data from an ultrasound scanner, the computer program product comprising a non-transient computer readable medium having computer readable program code embodied therein, the computer readable program code comprising: computer readable program code configured to generate at least one spatial coherence curve based on ultrasound backscatter data in the target region, the spatial coherence curve comprising coherence values as a function of depth in the sample; and computer readable program code configured to determine a property for a sample in response to the spatial coherence curve as a function of depth.

In some embodiments, the sample comprises in vivo liver tissue and the property comprises an estimation of fatty tissue or liver health.

In some embodiments, the estimation of fatty tissue or liver health is based on an experimental model of actual clinical data comprising spatial coherence curves for clinical values of fatty tissue or liver health.

In some embodiments, the estimation of fatty tissue or liver health indicates increased fatty tissue percentage or decreased liver health based on decreasing coherence values as a function of greater depth in the in vivo liver tissue.

In some embodiments, the computer program readable program code for determining a property for a sample in response to the spatial coherence curve as a function of depth further comprises computer readable program code for fitting a curve to the spatial coherence curve for the liver tissue, and the property is determined based on a correlation between a curve fit value and known curve fit values for the experimental model of actual clinical data.

In some embodiments, the estimation of fatty tissue or liver health comprises early stage steatosis.

In some embodiments, the experimental model of actual clinical data comprises a first set of spatial coherence curves for clinical values of fatty tissue or liver health corresponding to late-stage steatosis above a threshold steatosis value, and a second set of spatial coherence curves for clinical values of fatty tissue or liver health corresponding to early-stage steatosis below the threshold steatosis value, the computer readable program code further comprising computer readable program code for determining whether the sample is above or below the threshold steatosis value based on ultrasound elastography.

In some embodiments, the estimation of fatty tissue or liver health is determined based on the first set of spatial coherence curves if the ultrasound elastography indicates a steatosis value above the threshold steatosis value, and the estimation of fatty tissue or liver health is based on the second set of spatial coherence curves if the ultrasound elastography indicates a steatosis value below the threshold steatosis value.

In some embodiments, a system for determining a property for a sample having a target region using ultrasound data from an ultrasound scanner includes: an ultrasound transducer array configured to generate at least one spatial coherence curve based on ultrasound backscatter data in the target region, the spatial coherence curve comprising coherence values as a function of depth in the sample; and a signal analyzer configured to determine a property for a sample in response to the spatial coherence curve as a function of depth.

In some embodiments, the sample comprises in vivo liver tissue and the property comprises an estimation of fatty tissue or liver health.

In some embodiments, the estimation of fatty tissue or liver health is based on an experimental model of actual clinical data comprising spatial coherence curves for clinical values of fatty tissue or liver health.

In some embodiments, the estimation of fatty tissue or liver health indicates increased fatty tissue percentage or decreased liver health based on decreasing coherence values as a function of greater depth in the in vivo liver tissue.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS OF THE INVENTION

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. For example, the term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Embodiments according to the present invention are described herein with reference to the term "tissue." It will be understood that the term tissue can include biological materials, such as, blood, organs, vessels, and other biological objects found in a body. It will be further understood that embodiments according to the present invention may be applicable to humans as well as other species. Embodiments according to the present invention may also be utilized to image objects other than tissue.

It will be understood that the scope of the present invention includes, for example, two dimensional (2D) ultrasound imaging and 3D (or volumetric) ultrasound imaging. In addition, the components of the ultrasound imaging described herein may be packaged as a single unit or packaged separately and interconnected to provide the functions described herein.

Figure 1:
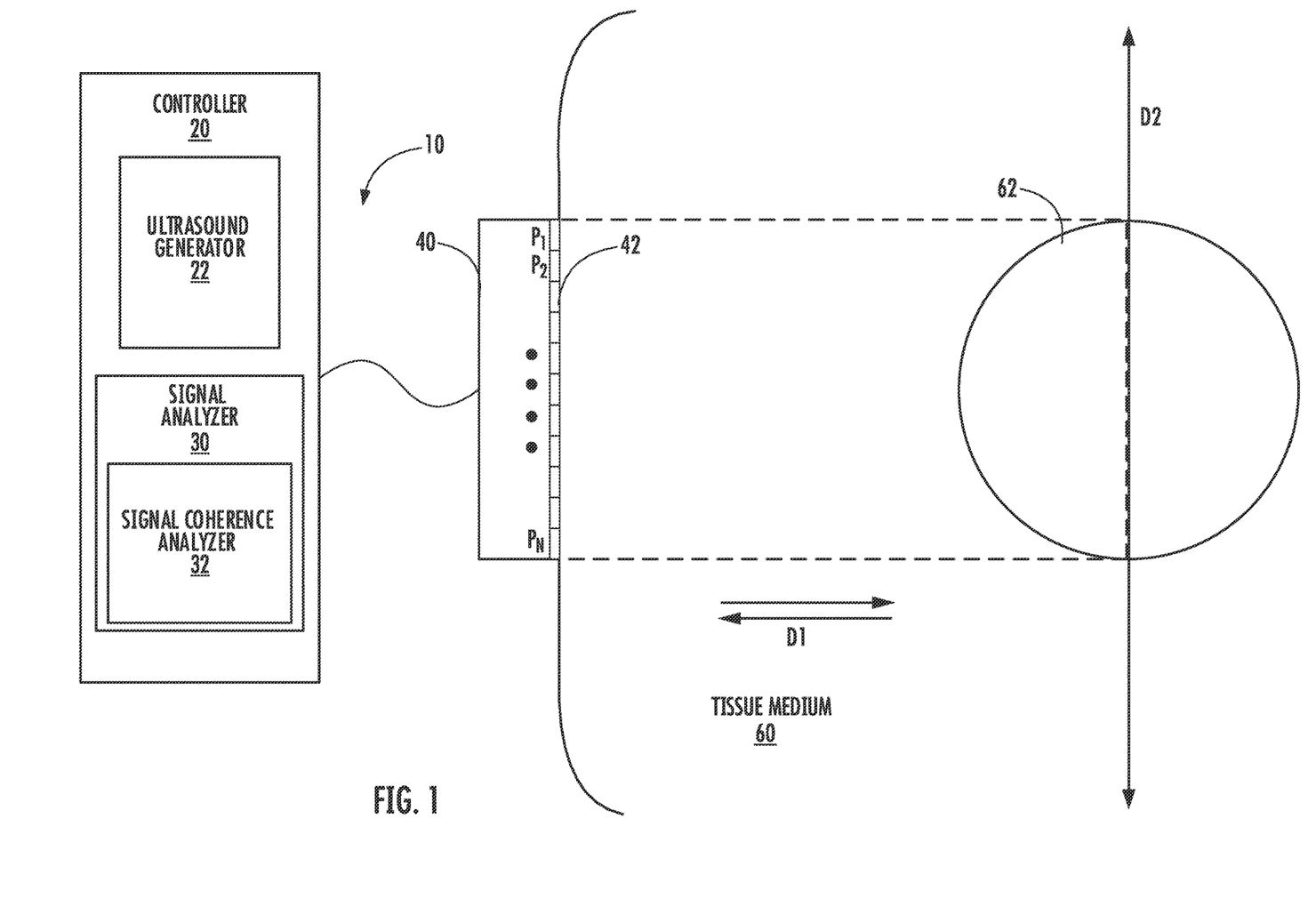
FIG. 1 is a schematic diagram of ultrasound systems, methods and computer program products according to some embodiments.

As illustrated in FIG. 1, an ultrasound system 10 includes a controller 20, a signal analyzer 30 and an ultrasound transducer array 40. The ultrasound transducer array 40 may include a plurality of array elements 42 at positions $P_1$ through $P_N$. The array elements 42 are configured to transmit and receive ultrasound signals 50 and may be contacted to a target medium such as a tissue medium 60. As illustrated, the tissue medium 60 includes a target region 62. The ultrasound array 40 may include ultrasound array elements 42 that define transmit/receive locations for transmitting and receiving ultrasound signals along a direction D1. In some embodiments, the array 40 may be configured to transmit sufficient ultrasound energy, for example, by applying an impulse excitation acoustic radiation force to the medium 60, to generate a shear wave that propagates in a direction D2 that is orthogonal to D1. The array 40 may also be configured to interrogate the tissue medium 60, for example, using ARFI or B-mode imaging techniques to monitor the tissue through time before and/or after the shear wave excitation force has been applied. ARFI imaging is discussed in U.S. Pat. Nos. 6,371,912; 6,951,544 and 6,764,448, the disclosures of which are hereby incorporated by reference in their entireties. Shear waves are discussed in U.S. Pat. Nos. 8,118,744 and 6,764,448, the disclosures of which are hereby incorporated by reference in their entireties. The ultrasound transducer array 40 may be a one-dimensional array configured to generate two-dimensional images or the ultrasound transducer array 40 may be a two-dimensional array configured to generate three-dimensional images.

The controller 20 may include an ultrasound generator 22 for sending and receiving ultrasound signals from the transducer array 40, and the signal analyzer 30 may include a coherence signal analyzer 32. The ultrasound generator 22 and the coherence signal analyzer 32 may be configured to control the array 40 and/or to analyze echo signals received by the array 40 as described herein. The ultrasound generator 22 and the coherence signal analyzer 32 may include hardware, such as control and/or analyzing circuits, and/or software stored on a non-transient computer readable medium for carrying out operations described herein.

Figure 2:
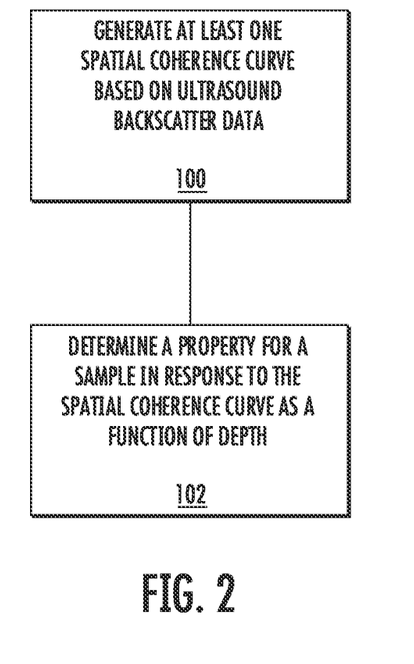
FIGS. 2-3 are flowcharts illustrating operations according to some embodiments.

As shown in FIG. 2, a property for a sample having a target region is determined using ultrasound data from the ultrasound scanner or transducer array 40 to generate at least one spatial coherence curve based on ultrasound backscatter data in the target region (Block 100). The spatial coherence curve includes coherence values as a function of depth in the sample. A property for a sample can be determined in response to the spatial coherence curve as a function of depth (Block 102).

Figure 3:
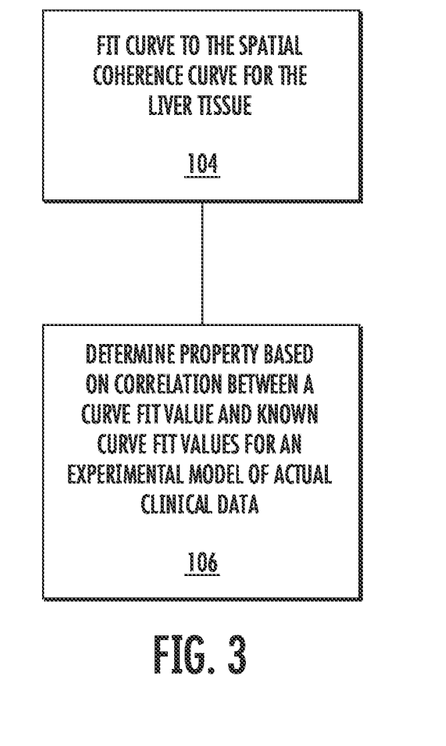
Figure 4A:
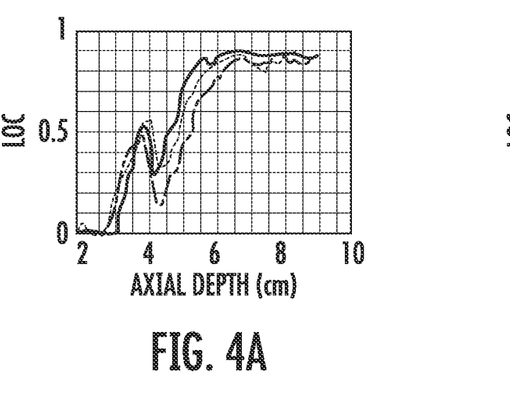
FIG. 4A-4L are axial Lag-One Coherence curves of liver tissue for different subjects according to some embodiments.
Figure 4B:
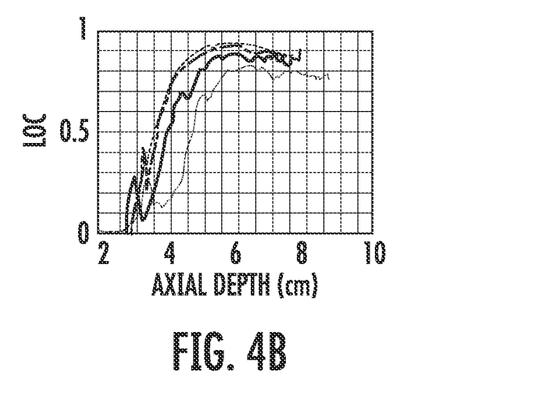
Figure 4C:
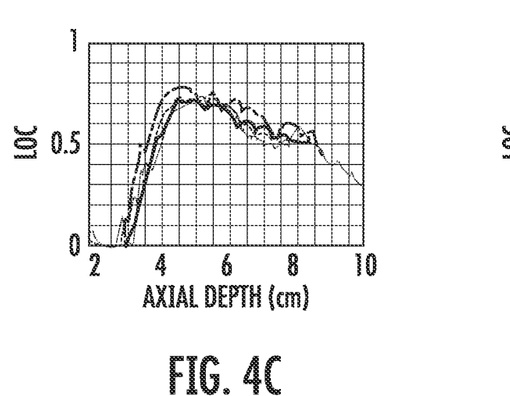
Figure 4D:
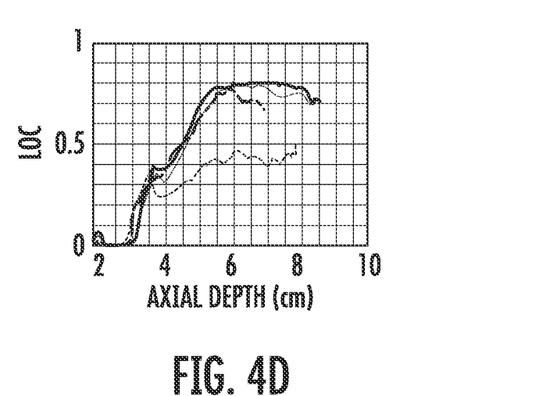
Figure 4E:
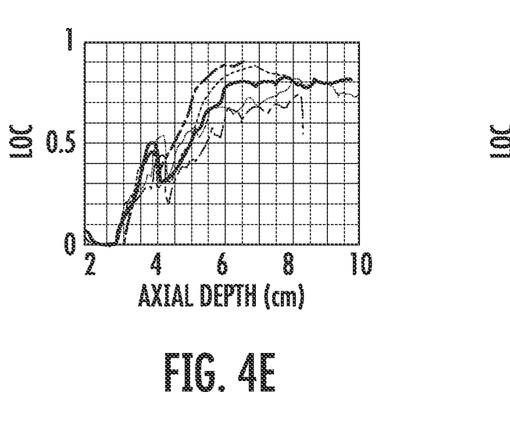
Figure 4F:
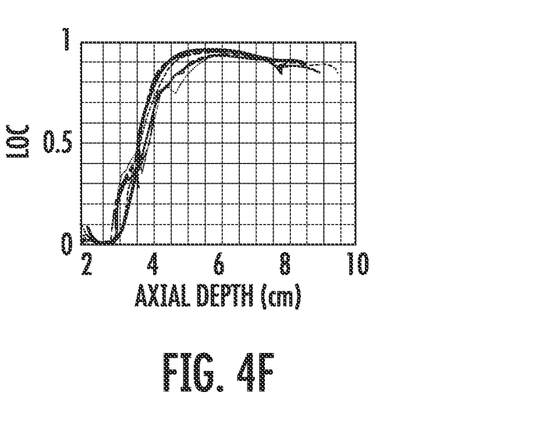
Figure 4G:
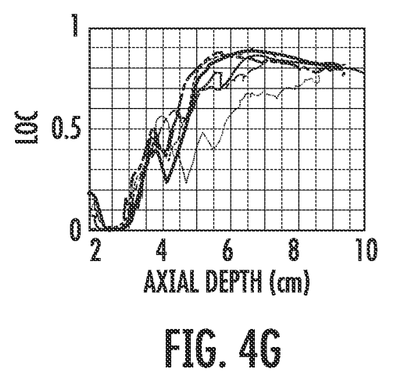
Figure 4H:
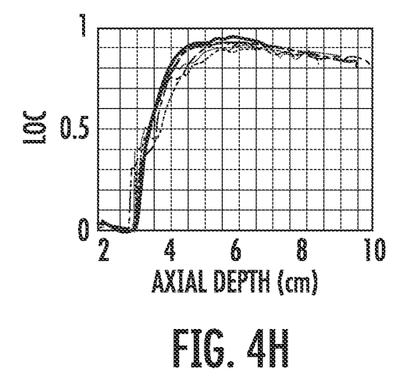
Figure 4I:
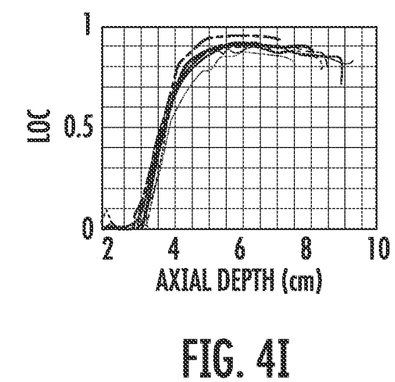
Figure 4J:
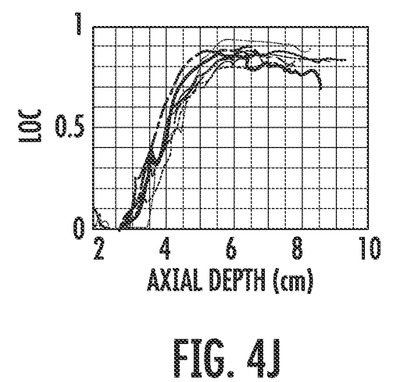
Figure 4K:
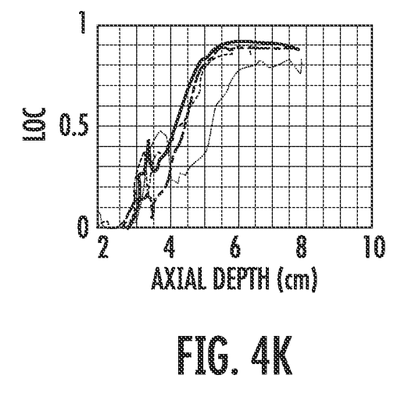
Figure 4L:
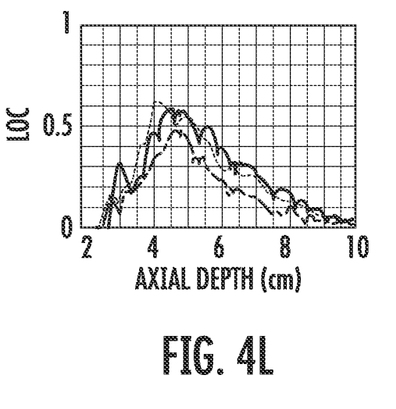

In some embodiments, the sample comprises in vivo liver tissue and the property comprises an estimation of fatty tissue or liver health. The estimation of fatty tissue or liver health may be based on an experimental model of actual clinical data comprising spatial coherence curves for clinical values of fatty tissue or liver health. The estimation of fatty tissue or liver health can indicate increased fatty tissue percentage or decreased liver health based on decreasing coherence values as a function of greater depth in the in vivo liver tissue. For example, as shown in FIG. 3, determining a property for a sample in response to the spatial coherence curve as a function of depth further can include fitting a curve to the spatial coherence curve for the liver tissue (Block 104), and the property is determined based on a correlation between a curve fit value and known curve fit values for the experimental model of actual clinical data (Block 106).

Any suitable spatial coherence values may be used. In some embodiments, the echo signals may be processed with a bandpass filter to obtain frequencies with the highest spatial coherence, and the filtered frequencies may be used for special coherence curves including the filtered coherence values as a function of depth in the sample.

In some embodiments, the estimation of fatty tissue or liver health may include early stage steatosis. Accordingly, steatosis may be detected at earlier stages than with conventional ultrasound techniques.

Various types of experimental data may be used to quantify the slope curves of coherence data, including slopes for known stages of fatty tissue for correlating slope curves to fatty tissue percentage or disease state. The data may be from actual clinical data in live subjects or calculated based on modeling techniques. In some embodiments, an experimental model of actual clinical data is used and includes a first set of spatial coherence curves for clinical values of fatty tissue or liver health corresponding to late-stage steatosis above a threshold steatosis value, and a second set of spatial coherence curves for clinical values of fatty tissue or liver health corresponding to early-stage steatosis below the threshold steatosis value. Whether a given sample is above or below the threshold steatosis value may be determined based on ultrasound elastography. For example, an estimation of fatty tissue or liver health may be determined if the ultrasound elastography indicates a steatosis value above or below a threshold steatosis value.

In some embodiments, spatial coherence curves may be used to estimate a percentage of fatty tissue in the sample or to estimate a stage of disease (typically stage 1-4) based on spatial coherence curves for tissue samples or experimental models with known fatty tissue content or known stages of disease.

The spatial decorrelation may be determined as a function of axial depth using any suitable spatial coherence metric, including but not limited to Lag-One Coherence (LOC), Short-Lag Spatial Coherence (SLSC), Generalized Coherence Factor GCF, beamformer gain, Phase Coherence Factor, a reciprocity method, and an angular coherence method.

For example, the van Cittert-Zernike (VCZ) is a theorem from statistical optics which describes the spatial coherence of an incoherent optical source. See J. W. Goodman, *Statistical optics*. John Wiley & Sons, 2015. Mallart and Fink have extended this theory to pulse-echo ultrasound, showing that the spatial coherence of backscattered echos echos from a diffuse scattering medium (such as liver tissue) is the Fourier transform of the transmit intensity distribution at the focus. See R. Mallart and M. Fink, "The van Cittert-Zernike theorem in pulse echo measurements," The Journal of the Acoustical Society of America, vol. 90, no. 5, pp. 2718{2727, 1991. For example, a rectangular source produces a sinc transmit intensity distribution at the focal depth, thereby predicting a triangular spatial coherence prole. In pulse echo ultrasound, this spatial coherence can be calculated by measuring the averaged normalized cross correlation between channel pairs separated by a varying number of channels (referred to as lags). The normalized spatial coherence R between Gaussian zero-mean complex echo signals S from channels i and i+m, with an element separation m, can be expressed as $$R_S[m] = \frac{\langle (S_i)(S_{i+m})^* \rangle}{\sqrt{\langle |S_i|^2 \rangle \langle |S_{i+m}|^2 \rangle}}, \quad (1)$$

where <.> represents the expected value and * represents the complex conjugate.

The expected value of the cross correlation can be modified to account for the presence of additive noise as $$R_{S+N}[m] = \frac{\langle (S_i + N_i)(S_{i+m} + N_{i+m})^* \rangle}{\sqrt{\langle |S_i + N_i|^2 \rangle \langle |S_{i+m} + N_{i+m}|^2 \rangle}}, \quad (2)$$

Where $N_i$ and $N_{i+m}$ represent additive noise for channels i and i+m.

Let $\psi_s$ and $\psi_N$ represent the power of the channel signals and noise, respectively, and the signal to noise ratio (SNR) be defined as $\psi_s/\psi_N$. Assuming uncorrelated noise N, expression for the spatial coherence of the combined signal and noise can be rewritten in terms of the signal to noise ratio and the noise-free spatial coherence $R_x[m]$ where $$R_{S+N}[m] = \begin{cases} 1, & m = 0 \\ \frac{SNR_c}{1+SNR_c} R_S[m], & m \neq 0 \end{cases} \quad (3)$$

Eq. 3 shows that the effect of spatially incoherent clutter is to introduce a step discontinuity between lags 0 and 1, whose relative contributions to the total coherence function is determined by a nonlinear scaling of the channel SNR. Thus, the spatial coherence at lag 1 (hereby referred to as lag-one coherence or LOC) is an indirect metric of incoherent noise power in a signal. Major sources of incoherent noise in ultrasound signals are reverberation from layer structures and wavefront distortions (aberration) from sound speed inhomogeneity. Without wishing to be bound by any particular theory, it is currently believed that fatty livers may generate increased incoherent noise from both reverberation and aberration due to differences in the acoustic impedance and sound speed between liver tissue and fat.

A simulation tool, Fullwave (developed by Pinton et al.) was used to generate RF data for the backscattered echoes resulting from acoustic propagation through a fatty medium. This software tool can accommodate arbitrary maps of acoustic parameters including sound speed, density, nonlinearity, and density. These acoustic parameters have been experimentally measured for both liver and fat tissue. The values of these acoustic maps can be tuned to mimic uniform liver with fat droplets of different sizes, concentrations and distributions. This allows for simulations of different degrees and presentations of liver steatosis. The spatial decorrelation in the aperture domain can then be assessed through a variety of spatial coherent metrics, including, but not limited to Lag-One Coherence (LOC), Short-Lag Spatial Coherence (SLSC), Generalized Coherence Factor GCF, beamformer gain, Phase Coherence Factor, a reciprocity method (see Nick Bottenus, Kutay F Üstüner, IEEE Trans Ultrason Ferroelectr Freq Con 2015 May; 62(5):852-61) and an angular coherence method (see J Acoust Soc Am2017 Mar; 141(3):1582). In addition, the relative contributions of reverberation clutter and phase aberration can be parsed from the spatial coherence curve, using theory introduced by Walker and Trahey for the distortions introduced by aberration and incoherent noise. See W. F. Walker and G. E. Trahey, "Speckle Coherence and Implications for Adaptive Imaging," Journal of the Acoustical Society of America, vol. 101, no. 4, pp. 1847{1858, 1997, issn: 0001-4966. doi: https://doi.org/10.1121/1.418235.

In some embodiments, one or more spatial coherence curves based on ultrasound backscatter data in the tissue ("target region") that includes coherence values as a function of depth may be used to estimate liver health. However, it should be understood that the spatial coherence curves described herein may be combined with other data, including additional ultrasonic elastography methods, which may improve fibrosis assessment and increase sensitivity and specificity in detecting advanced fibrosis. Conventional ultrasound typically utilizes image brightness to detect steatosis, but is a subjective measurement and may be insensitive to early disease stages. By adding a quantitative measure of steatosis to ultrasonic imaging studies, such as the spatial coherence curves described herein, it may be possible to better discriminate SS from NASH and better detect early stages of NAFLD. In some embodiments, 100% sensitivity and 91% specificity may be achieved.

Liver Spatial Coherence

Ultrasound scans were used to generate a spatial coherence curve based on ultrasound backscatter data for subjects with presumed healthy livers to measure the liver spatial coherence. Data was also acquired from two subjects with known fatty liver disease. The axial LOC curves as a function of axial depth for each subject is shown in FIGS. 4A-4L. In the presumed healthy livers, there is an initial region of suppressed coherence due to focusing errors and noise from the abdominal wall, followed by recovery to a high and relatively stable asymptotic LOC value, e.g., for axial depths greater than about 4 cm to 6 cm. However, in the two patients with known fatty liver disease, the depth-dependence of the LOC curve is measurably different from presumed healthy livers. In patients with known fatty liver disease, the LOC curve maximizes at lower values of depth, and is followed by a decrease with depth. In suspected normal patients, the spatial coherence remains relatively stable with axial range. The LOC curve pattern of decreased coherences as a function of depth is consistent across multiple independent acquisitions in both fatty liver patients and is not observed in any of the presumed healthy subjects over all acoustic windows that were interrogated, including both sub- and inter-costal positioning. The LOC curves for the two patients with known fatty liver disease are FIGS. 4C and 4L, which illustrate a pattern of decreased coherences as a function of depth.

Figure 5A:
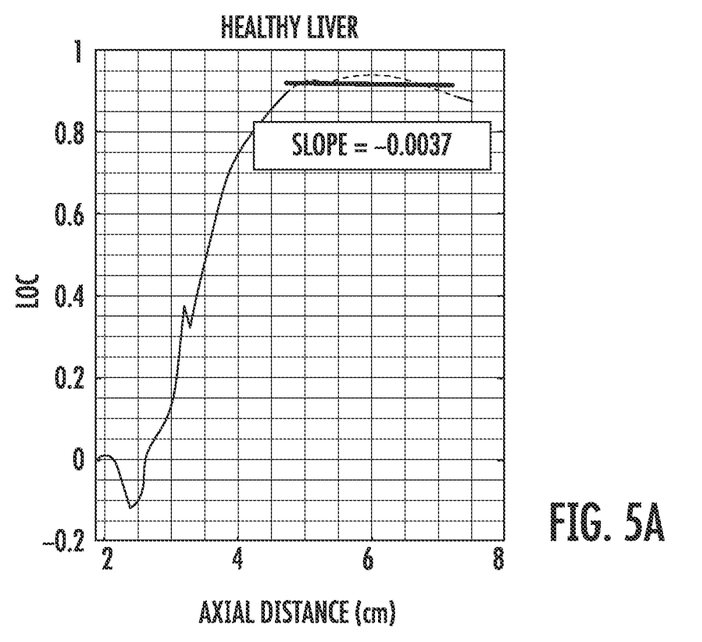
FIG. 5A is an example fit curve algorithm for the Lag-One Coherence curves for a healthy liver according to some embodiments.
Figure 5B:
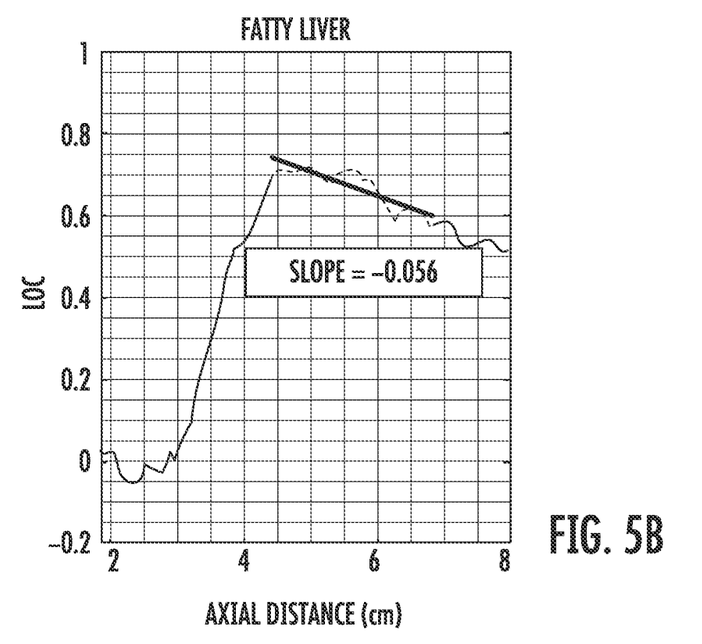
FIG. 5B is an example of a fit curve algorithm for the Lag-One Coherence curves for a fatty liver illustrating a greater slope than for the healthy liver of FIG. 5A according to some embodiments.

A metric for steatosis quantification is the slope of the line of best fit for the LOC as a function of depth, calculated starting at an axial depth where the LOC exceeds 95% of the maximum value and extending an additional 2.5 cm. FIG. 5A illustrates an example of the curve fitted for a presumed healthy volunteer subject. The fitted curve is illustrated as having a slope of 0.0037. Although the fit curve of FIG. 5A is illustrated over a 2.5 cm region, it should be understood that other regions may be selected. For example, fit curves may be created by laterally averaging manually selected regions of uniform liver tissue. A corresponding fit curve for a fatty liver is shown in FIG. 5B.

Figure 5C:
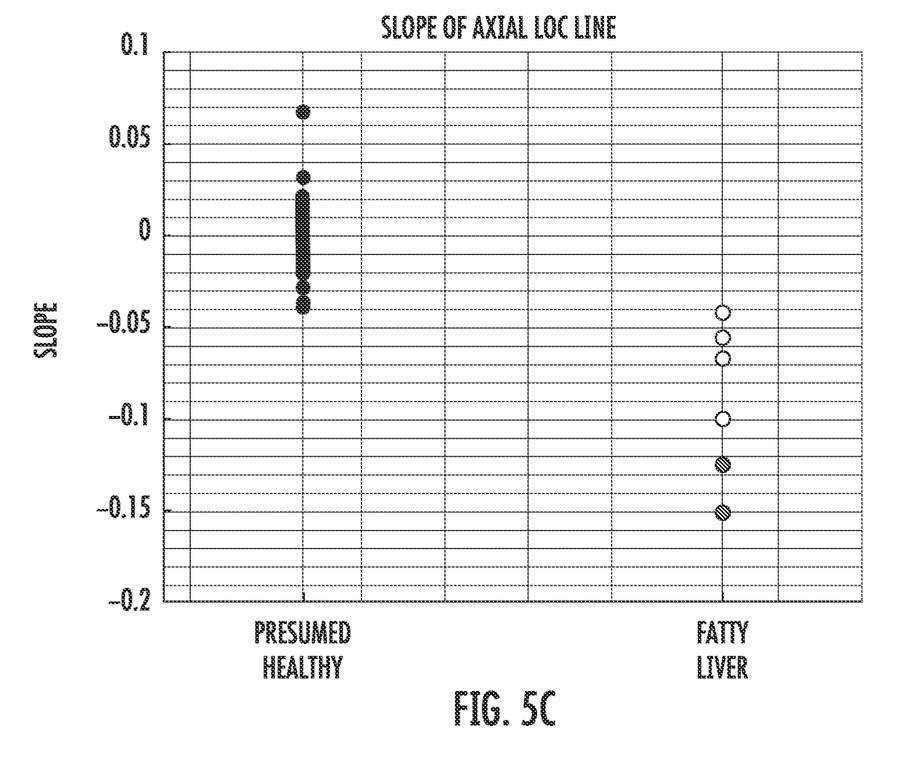
FIG. 5C is a graph of the separation between the slopes of coherence data for presumed healthy and fatty liver subjects according to some embodiments.

Separation between the slopes of fatty liver and presumed healthy subjects are demonstrated with only twelve subjects. Fatty liver subjects show large negative slopes compared to presumed healthy subjects having slopes centered around zero. The results are consistent across many acquisitions of data, and although limited in number, the patient group represents a wide range of patient ages and body habitus types. The separation between the slopes of presumed healthy and fatty liver subjects is shown in FIG. 5C. The mean slope in presumed healthy subjects is −0.0015±0.0164. The mean slope in fatty liver subjects is a much larger negative slope of −0.0992±0.0448.

Simulations

A finite difference acoustic simulation tool, Fullwave™ was used to replicate the pattern of axial LOC values seen in vivo for different fat concentrations. In particular, the fatty liver conditions show a lower peak LOC value, and a sharper downward slope after the peak compared to uniform conditions. Additionally, there are discernible differences in the curve slopes between different concentrations of fat, which indicates that different stages of steatosis may be estimated. In some embodiments, quantifying or estimating the concentration of fat based on the axial LOC curve may be achieved.

The simulations were performed in harmonic imaging mode using a 4.7 MHz frequency with 80% bandwidth, which are transmit conditions that match those used to collect the in vivo data. The curves reach lower peaks and have steeper downward slopes as the fat percentage increases from 5% to 40%. The 70% fat condition shows an increase in peak LOC with a shallower slope compared to 20% and 50% conditions. Additional research may determine why the trend of lower LOC values and more negative slopes do not occur for the 70% fat condition in the simulation. However, for high fat content, the liver may be more uniform due to the very high percentage of fat.

Figure 6:
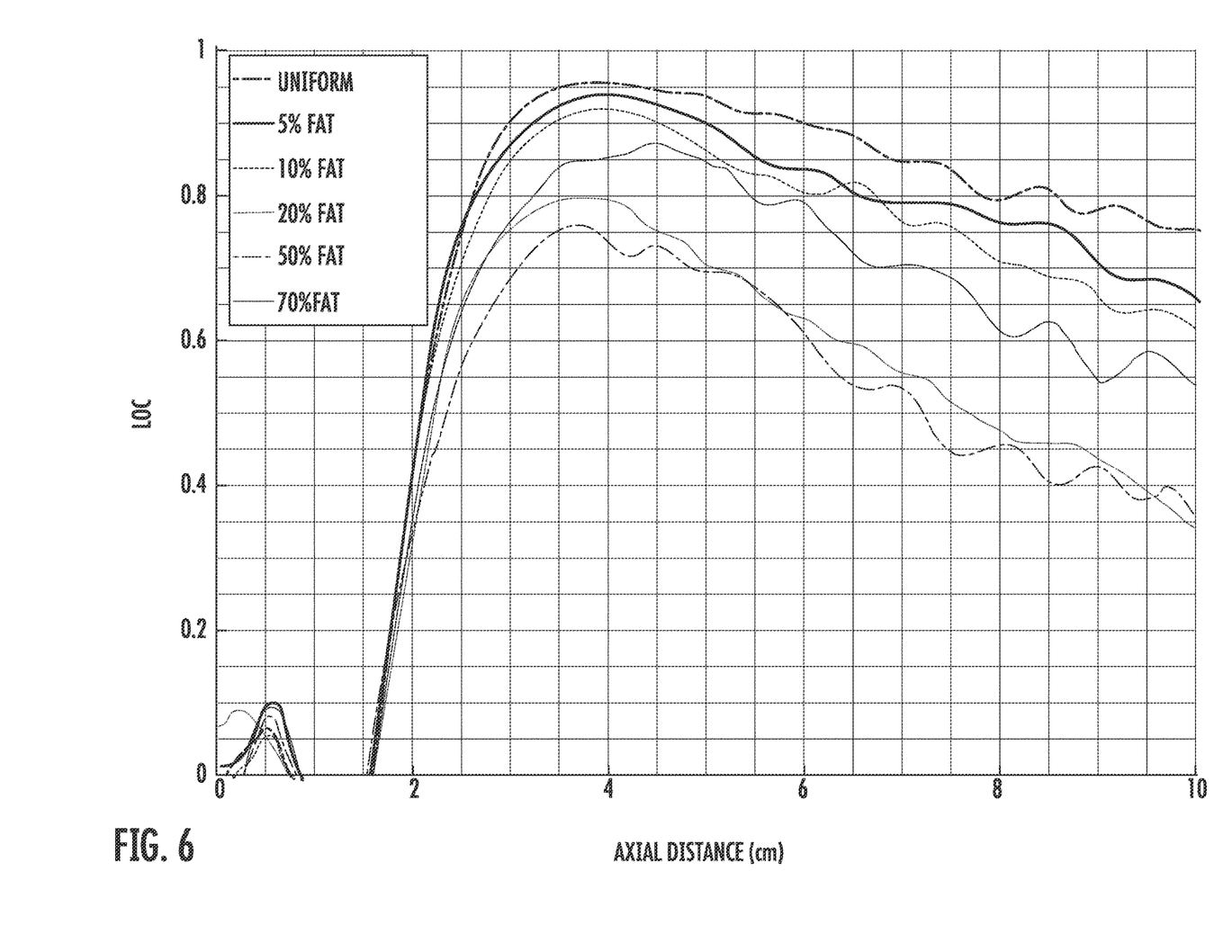
FIG. 6 is a graph of the Lag-One Coherence curves for different fat concentrations according to some embodiments.

FIG. 6 is a graph of axial LOC for different fat concentrations. LOC values are calculated with a $5\lambda$ kernel and a 0.5 cm smoothing filter was applied to the resultant lines. These trends replicate that seen in vivo, with lower LOC values that have a steeper downward slope as a function of axial distance or depth into the tissue indicating increased fatty liver conditions.

Accordingly, adjustments to the estimation of liver fat percentage may be used for livers with a very high percentage of fat, such as combining the slope of the LOC values with other data, such as conventional ultrasound imaging used for screening of suspected NAFLD include evaluating liver stiffness using ultrasound elastography, including strain elastography and shear wave elastography, which uses acoustic radiation force induced tissue displacement. In addition to elastography methods, other conventional ultrasound methods for estimating fat content include estimations of backscatter brightness, the controlled attenuation parameter, or the sound speed. For example, if conventional ultrasound imaging for screening suspected NAFLD indicates a high likelihood of NAFLD, a different relationship between the slope of the coherence values may be used. Other data that may be combined with the coherence curves include fundamental or harmonic imaging or a combination of ultrasound imaging techniques. In addition, non-ultrasound data may also be combined to the coherence curves described herein, such as body mass index, MRI scans, and liver blood tests or panels.

In some embodiments, early stages of steatosis with smaller fat percentages may be detected based on the slope of the LOC curves. Estimation of fatty tissue or liver health may be based on an experimental model of actual clinical data including spatial coherence curves for clinical values of fatty tissue or liver health. For example, liver fat fractions of as low as between 5% and 30% (or stage 1 NAFLD) may be detected. However, higher percentages of fat fractions greater than 30%, or greater than 50%, may also be detected based on the slope of the LOC curves alone or combined with other NAFLD evaluation data, such as conventional ultrasound imaging data.

In some embodiments, a patient may be screened using conventional NAFLD detection methods, which are generally useful in detecting later stages of steatosis. If a later stage of steatosis is not detected, then the slope of the LOC curve may be used to detect or evaluate the probability that the patient has early stage steatosis, such as fat percentages below 30%, below 40% or below 50%.

In some embodiments, LOC data may be correlated with estimates of liver fat content, liver stiffness, and/or liver attenuation by using biopsy-derived measurements of fat content, fibrosis, and inflammation. Biopsy data may be determined, for example, using a METAVIR score, which can be used to distinguish between normal liver (stage 0) to cirrhosis. Other ultrasound-derived parameters may also be used, such as shear velocity, attenuation, backscatter strength, and the axial spatial coherence profile. The intra-patient variability of the ultrasound metrics may be calculated. The patients' BMI, abdominal thickness (from ultrasound), age and gender may also be used.

Although embodiments of the current invention are described with respect to a linear fit curve, other types of curve fits may be used, such as high order polynomials, exponential, and logarithmic fits. Any suitable curve fit may be used to correlate with or estimate liver health or liver metrics, such as fat percentage or stage of steatosis. Various metrics may be used, such as peak LOC and slope, and correlated with known parameters, such as fat content and METAVIR score or conventional ultrasound-related metrics.

In some embodiments, the correlation of coherence data with estimates of liver fat content or other estimates of liver health using convention techniques may be used to develop a database or other parameters to estimate liver fat content, steatosis or other metrics of liver health using LOC data alone or in combination with other data, such as noninvasively determine data.

In some embodiments, coherence artifacts near the liver capsule and blood vessels or other conditions may be used to void particular datasets or to signal to a user or health care professional that different datasets should be acquired, such as from a different region of the liver.

The spatial coherence data data may be combined with conventional ultrasound measurements to determine a measurement of liver fat, including mechanical parameter(s) of the sample, such as shear elasticity modulus, Young's modulus, storage modulus dynamic shear viscosity, shear wave velocity and mechanical impedance, which can be correlated to measurement of healthy/diseased tissue states, such as by using actual clinical data and known healthy/diseased tissue states. The clinical data can be based on other factors such as demographic information, e.g., age, gender and race, to correlate the measurement of the mechanical parameter(s) with a measurement of healthy/diseased tissue states in a particular demographic group.

In some embodiments, estimates of the health of the tissue can be monitored as a function of time by performing the analyzing techniques described herein on a subject repeatedly over a period of time. A healthy/diseased tissue state determination can be based on a change in the spatial coherence values as a function of time. For example, the spatial coherence values can be monitored over a period of minutes, hours, days, weeks, months or even years to determine the progression of the disease and/or the efficacy of treatment.

The spatial coherence data may be generated as described herein with an internally inserted ultrasound probe array or an externally applied ultrasound array. In some embodiments, the target region may be an in vivo human tissue sample; however, in vitro biomaterials, such as engineered tissues or hydrogels may be used.

Although embodiments according to the present invention are described with respect to Lag-One Coherence (LOC) data, it should be understood that any suitable coherence data may be used, including Short-Lag Spatial Coherence (SLSC), Generalized Coherence Factor GCF, beamformer gain, Phase Coherence Factor, a reciprocity method and an angular coherence method. In order to extend the axial range over which spatial coherence might be calculated without degradation from transmit focal errors, a swept transmit focus or synthetic transmit aperture method may be used.

Moreover, although embodiments are described with respect to liver tissue, other tissue samples may be used. In vivo and ex vivo samples may be analyzed. Non-medical applications are also contemplated, such as measuring the fat content (i.e., a degree of marbling) of beef or other meets before or after slaughter. Spatial coherence curves may be used to monitor or evaluate other food products, such as to monitor the ripening of cheese over time. For example, spatial coherence curves could be measured over the cheese making process to determine a curve that correlates with ripening stages of the cheese. The foregoing is illustrative of the present invention and is not to be construed as limiting thereof. Although a few example embodiments of this invention have been described, those skilled in the art will readily appreciate that many modifications are possible in the example embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for determining a property for a sample having a target region using ultrasound data from an ultrasound scanner, the method comprising:
    transmitting an ultrasound signal from an ultrasound transducer array having a plurality of array elements in the target region;
    receiving ultrasound echo signals at the ultrasound transducer array to provide ultrasound backscatter data in the target region;
    generating a plurality of spatial coherence values in the target region based on the ultrasound backscatter data that correspond to a plurality of tissue depths in the target region;
    generating at least one spatial coherence curve based on the plurality of spatial coherence values for the ultrasound backscatter data in the target region, the at least one spatial coherence curve comprising the plurality of spatial coherence values as a function of depth in the sample; and determining the property for the sample using the at least one spatial coherence curve as a function of depth,
wherein the sample comprises in vivo liver tissue of a patient and the property comprises an estimation of fatty tissue or liver health for treating the patient based on the estimation of fatty tissue or liver health.

2. The method of claim 1, wherein the estimation of fatty tissue or liver health is based on an experimental model of actual clinical data comprising a plurality of previous spatial coherence curves corresponding to clinical values of fatty tissue or liver health.

3. The method of claim 2, wherein the estimation of fatty tissue or liver health indicates increased fatty tissue percentage or decreased liver health based on the spatial coherence values decreasing as a function of greater depth in the in vivo liver tissue.

4. The method of claim 3, wherein determining the property for the sample in response to the at least one spatial coherence curve as a function of depth further comprises fitting a curve to the at least one spatial coherence curve for the liver tissue, and the property is determined based on a correlation between a curve fit value and known curve fit values for the experimental model of actual clinical data.

5. The method of claim 4, wherein the estimation of fatty tissue or liver health comprises early stage steatosis.

6. The method of claim 4, wherein the experimental model of actual clinical data comprises a first set of previous spatial coherence curves for clinical values of fatty tissue or liver health corresponding to late-stage steatosis above a threshold steatosis value, and a second set of previous spatial coherence curves for clinical values of fatty tissue or liver health corresponding to early-stage steatosis below the threshold steatosis value, the method further comprising determining whether the sample is above or below the threshold steatosis value based on ultrasound elastography.

7. The method of claim 6, wherein the estimation of fatty tissue or liver health is determined based on the first set of previous spatial coherence curves if the ultrasound elastography indicates a steatosis value above the threshold steatosis value, and the estimation of fatty tissue or liver health is based on the second set of previous spatial coherence curves if the ultrasound elastography indicates a steatosis value below the threshold steatosis value.

8. A computer program product for determining a property for a sample having a target region using ultrasound data from an ultrasound scanner, the computer program product comprising anon-transient computer readable medium having computer readable program code embodied therein, the computer readable program code comprising:
computer readable program code configured to control an ultrasound transducer array having a plurality of array elements to transmit an ultrasound signal in the target region;
computer readable program code configured to control the ultrasound transducer array to receive ultrasound echo signals to provide ultrasound backscatter data in the target region;
computer readable program code configured to generate a plurality of spatial coherence values based on the ultrasound backscatter data in the target region that correspond to a plurality of tissue depths in the target region;
computer readable program code configured to generate at least one spatial coherence curve based on the plurality of spatial coherence values for the ultrasound backscatter data in the target region, the spatial coherence curve comprising the plurality of spatial coherence values as a function of depth in the sample; and
computer readable program code configured to determine the property for the sample using the spatial coherence curve as a function of depth,
wherein the sample comprises in vivo liver tissue of a patient and the property comprises an estimation of fatty tissue or liver health for treating the patient based on the estimation of fatty tissue or liver health.

9. The computer program product of claim 8, wherein the estimation of fatty tissue or liver health is based on an experimental model of actual clinical data comprising a plurality of previous spatial coherence curves for clinical values of fatty tissue or liver health.

10. The computer program product of claim 9, wherein the estimation of fatty tissue or liver health indicates increased fatty tissue percentage or decreased liver health based on the spatial coherence values decreasing as a function of greater depth in the in vivo liver tissue.

11. The computer program product of claim 10, wherein the computer program readable program code for determining the property for the sample in response to the at least one spatial coherence curve as a function of depth further comprises computer readable program code for fitting a curve to the at least one spatial coherence curve for the liver tissue, and the property is determined based on a correlation between a curve fit value and known curve fit values for the experimental model of actual clinical data.

12. The computer program product of claim 11, wherein the estimation of fatty tissue or liver health comprises early stage steatosis.

13. The computer program product of claim 11, wherein the experimental model of actual clinical data comprises a first set of previous spatial coherence curves for clinical values of fatty tissue or liver health corresponding to late-stage steatosis above a threshold steatosis value, and a second set of previous spatial coherence curves for clinical values of fatty tissue or liver health corresponding to early-stage steatosis below the threshold steatosis value, the computer readable program code further comprising computer readable program code for determining whether the sample is above or below the threshold steatosis value based on ultrasound elastography.

14. The computer program produce of claim 13, wherein the estimation of fatty tissue or liver health is determined based on the first set of spatial coherence curves if the ultrasound elastography indicates a steatosis value above the threshold steatosis value, and the estimation of fatty tissue or liver health is based on the second set of spatial coherence curves if the ultrasound elastography indicates a steatosis value below the threshold steatosis value.

15. A system for determining a property for a sample having a target region using ultrasound data from an ultrasound scanner, the system comprising:
an ultrasound transducer array having a plurality of array elements configured to transmit an ultrasound signal from the ultrasound transducer array in the target region; to receive ultrasound echo signals at the ultrasound transducer array to provide ultrasound backscatter data in the target region; and
a signal analyzer configured to generate a plurality of spatial coherence values in the target region based on the ultrasound backscatter data that correspond to a plurality of tissue depths in the target region, to generate at least one spatial coherence curve based on the plurality of spatial coherence values for the ultrasound backscatter data in the target region, the spatial coherence curve comprising the plurality of spatial coherence values as a function of depth in the sample and to determine the property for the sample using to the spatial coherence curve as a function of depth;

wherein the sample comprises in vivo liver tissue of a patient and the property comprises an estimation of fatty tissue or liver health for treating the patient based on the estimation of fatty tissue or liver health.

16. The system of claim 15, wherein the estimation of fatty tissue or liver health is based on an experimental model of actual clinical data comprising a plurality of previous spatial coherence curves for clinical values of fatty tissue or liver health.

17. The system of claim 16, wherein the estimation of fatty tissue or liver health indicates increased fatty tissue percentage or decreased liver health based on the spatial coherence values decreasing as a function of greater depth in the in vivo liver tissue.

* * * * *